US011217334B2

(12) United States Patent
Netzer et al.

(10) Patent No.: US 11,217,334 B2
(45) Date of Patent: Jan. 4, 2022

(54) SYSTEM AND METHOD FOR SELECTING OPTIMAL MEDICATIONS FOR A SPECIFIC PATIENT

(71) Applicant: MOR RESEARCH APPLICATIONS LTD, Tel Aviv (IL)

(72) Inventors: Doron Netzer, Zichron Yaakov (IL); Dan Nabriski, Raanana (IL); Eytan Roitman, Nordiya (IL)

(73) Assignee: MOR RESEARCH APPLICATIONS LTD.

( * ) Notice: Subject to any disclaimer, the term of this patent is extended or adjusted under 35 U.S.C. 154(b) by 317 days.

(21) Appl. No.: 16/073,484

(22) PCT Filed: Feb. 27, 2017

(86) PCT No.: PCT/IL2017/050246
§ 371 (c)(1),
(2) Date: Jul. 27, 2018

(87) PCT Pub. No.: WO2017/149530
PCT Pub. Date: Sep. 8, 2017

(65) Prior Publication Data
US 2019/0035496 A1 Jan. 31, 2019

Related U.S. Application Data

(60) Provisional application No. 62/300,931, filed on Feb. 29, 2016.

(51) Int. Cl.
*G16H 10/60* (2018.01)
*G16H 70/40* (2018.01)
(Continued)

(52) U.S. Cl.
CPC ............. *G16H 10/60* (2018.01); *G16H 20/10* (2018.01); *G16H 50/20* (2018.01); *G16H 70/40* (2018.01)

(58) Field of Classification Search
CPC ........ G16H 50/20; G16H 10/60; G16H 50/70; G16H 50/50; G16H 15/00; G16H 50/30;
(Continued)

(56) References Cited

U.S. PATENT DOCUMENTS 7,617,519 B2   11/2009   Williams
7,698,157 B2    4/2010   Ghouri
(Continued)

OTHER PUBLICATIONS

Aljaaf et al., "Toward an optimal use of artificial intelligence techniques within a clinical decision support system," 2015 Science and Information Conference (SAI), Jun. 30, 2015, pp. 548-554, doi: 10.1109/SAI.2015.7237196. (Year: 2015).*
Wiesner et al., "Health recommender systems: concepts, requirements, technical basics and challenges," International Journal of Environmental Research and Public Health, vol. 11(3), pp. 2580-2607, Mar. 3, 2014, doi:10.3390/ijerph110302580. (Year: 2014).*
International Search Report PCT/IL2017/050246 Completed May 16, 2017; dated Jun. 21, 2017 3 pages.
International Search Report PCT/IL2017/050246 dated Jun. 21, 2017 7 pages.

*Primary Examiner* — Joy Chng
(74) *Attorney, Agent, or Firm* — The Roy Gross Law Firm, LLC; Roy Gross

(57) ABSTRACT

Embodiments disclosed herein relate to a computerized method of selecting an optimal medication for a patient, comprising: providing a user with communication access to a central server having in memory a database of a rule set associated with a list of medications available, the rules set numerically ranking the suitability of a medication for a patient; allowing upload of at least a portion of an electronic medical record for an identified patient; allowing input of a patient diagnosis, and receiving a search request for a suitable treatment medication; comparing the rules set, with the uploaded electronic medical record; determining (e.g., scoring and calculating) the suitability of medications from the list of medications available; providing a displayable list of medications suited for the patient, wherein the list is ranked according to the preference of the medications for the patient.

18 Claims, 5 Drawing Sheets

(51) Int. Cl.
*G16H 50/20* (2018.01)
*G16H 20/10* (2018.01)

(58) Field of Classification Search
CPC ........ G16H 30/20; G16H 30/40; G16H 20/10; G16H 40/60; G16H 10/20; G16H 40/63; G16H 10/65; G16H 20/13; G16H 40/20; G16H 20/17; G16H 50/80; G16H 70/20; G16H 70/60; G16H 80/00; G16H 20/00; G16H 20/60; G16H 20/70; G16H 40/67; G16H 70/00; G16H 70/40; G06Q 50/22; G06Q 50/24; G06Q 10/10; G06Q 30/02; G06Q 30/0283; G06Q 40/08; G06Q 50/01; G06Q 10/00; G06Q 10/04; G06Q 10/06; G06Q 10/063; G06Q 10/0633; G06Q 10/103; G06Q 10/107; G06Q 20/085; G06Q 20/102; G06Q 30/0207; G06Q 30/0241; G06Q 30/0269; G06Q 30/04; G06Q 30/0603; G06Q 50/18; G06Q 50/205; G06Q 50/2057; G06Q 10/60; G06Q 20/10; G06Q 70/40; G06Q 50/20

USPC ........................................................ 705/2–3
See application file for complete search history.

(56) References Cited

U.S. PATENT DOCUMENTS

| | | | |
|---|---|---|---|
| 8,032,394 | B1 | 10/2011 | Ghouri |
| 8,155,993 | B2 | 4/2012 | de Nijs et al. |
| 8,407,069 | B2 | 3/2013 | Brown et al. |
| 8,489,416 | B2 | 7/2013 | McGuigan et al. |
| 8,589,175 | B2 | 11/2013 | Glauser et al. |
| 8,645,165 | B2 | 2/2014 | Belcher et al. |
| 8,700,430 | B2 | 4/2014 | Miller et al. |
| 8,762,164 | B2 | 6/2014 | McGuigan et al. |
| 2003/0171657 | A1* | 9/2003 | Leonard ................. G16H 20/10 600/300 |
| 2004/0162835 | A1* | 8/2004 | Ghouri ................... G16H 10/60 |
| 2008/0243548 | A1* | 10/2008 | Cafer ..................... G16H 15/00 705/3 |
| 2015/0039325 | A1 | 2/2015 | Longman et al. |

\* cited by examiner

MEDICAL CONDITION - SCREEN 1

DISEASE: ☐
DESCRIPTION: ☐

LINKING PARAMETERS TO A DISEASE
- ☑ AGE
- ☑ BMI
- ☑ HBA1C
- ☑ GFR
- ☑ POST PRAN
- ☑ FASTING
- ☑ HYPOGLY
- ☑ MED CA THY
- ☑ PANCREA
- ☑ GASTROPA

LINKING TREATMENT TO A DISEASE
- ☑ ACARBOSE
- ☑ ACTOS
- ☑ AMARYL
- ☑ BYETTA
- ☑ BYDUREON
- ☑ FORXIGA
- ☑ GALVUS
- ☑ GLUCORITE
- ☑ JANUVIA
- ☑ LYXUMIA

[ENTER RULES] [SAVE]

DOCTOR SCREEN - PATIENT PARAMETERS

SPECIFIC PATIENT PARAMETERS ARE ENTERED BY PHYSICIAN TO GENERATE A RECOMMENDED TREATMENT

| PARAMETER | |
|---|---|
| AGE | 58 |
| BMI | 32 |
| GFR | 75 |
| UTI (0/1) | 1 |
| PANCREA (0/1) | 0 |

[CALCULATE]

[RESTART]

*FIG. 7*

DOCTOR SCREEN - RECOMMENDATIONS

| PARAMETER | SCORE | |
|---|---|---|
| ○ TREATMENT D | 100 | RECOMMENDED |
| ○ TREATMENT C | 82 | RECOMMENDED |
| ○ TREATMENT A | 65 | SECONDARY RECOMMENDED |
| ○ TREATMENT F | 23 | CONTRAINDICATED |
| ○ TREATMENT B | 10 | CONTRAINDICATED |

[CORRECT]

[RESTART]

*FIG. 8*

MAIN ENTITIES

- MEDICAL CONDITION
- TREATMENTS
- PARAMETER
- RULESETS - COMBINATION OF TREATMENT AND PARAMETER FOR THE MEDICAL CONDITION

|  | ACARBOSE | | ACTOS | | AMARYL | | BYETTA | |
|---|---|---|---|---|---|---|---|---|
| AGE | 0 | | 0 | | 18-59<br>60+ | 0<br>-1 | 0 | |
| BMI | <27<br><30<br>30+ | 0<br>1<br>2 | <27 | -1 | <27<br><30<br>30+ | 0<br>-1<br>-2 | <25<br><27<br>27+ | 0<br>1<br>2 |
| HBA1C | <8<br><10<br>10+ | 0<br>-1<br>-2 | >7.5 | 1 | 0 | | <7.5<br>7.5+ | 0<br>2 |
| POST PRAN | YES | 2 | 0 | | YES | 2 | YES | 2 |

*FIG. 9*

SYSTEM AND METHOD FOR SELECTING OPTIMAL MEDICATIONS FOR A SPECIFIC PATIENT

CROSS-REFERENCE TO RELATED APPLICATIONS

This application is a National Phase of PCT Patent Application No. PCT/IL2017/050246 having International filing date of Feb. 21, 2017, which claims priority of U.S. Provisional Application No. 62/300,931 filed on Feb. 29, 2016 titled "Software For Selecting Optimal Medications For A Specific Patient". The contents of the above applications are all incorporated by reference as if fully set forth herein in their entirety

FIELD OF THE INVENTION

The present disclosure generally relates to computerized decision-support systems and methods and, more specifically, to computerized systems and methods for healthcare professionals.

BACKGROUND

A plethora of medications exists to treat common diseases such as diabetes and hypertension. These medications may differ in many factors such as dosage, length of effect, release time, mechanism, and known side effects.

Even when a diagnosis is immediately clear, a physician needs to spend several minutes of each patient visit reviewing the medical record to ensure the correct medication is prescribed. Medications typically have contraindications that limit prescription to patients who do not fit the recommended parameters, due to their overall medical condition, BMI, or blood test results such as kidney function, lipid profile, hemoglobin level, etc. Additionally, patients with chronic diseases may have a plurality of medical conditions that contraindicate prescription of one or more medications that would have otherwise been suitable. In today's HMO model of health care, physicians are required to limit the time spent with any individual patient. Other factors that can affect the selection of the most appropriate medication may be that medical boards in some countries place different emphasis on contraindications for specific medications. Cost may also be a factor in selecting a generic medication over a more expensive, original version. Each medication has advantages and disadvantages, which might not always be considered when choosing the best treatment. Related art documents include: U.S. Pat. Nos. 8,155,993 and 8,032,394.

Acknowledgement of the above related art documents is not to be inferred as meaning that these are in any way relevant to the patentability of the presently disclosed subject matter.

The description above is presented as a general overview of related art in this field and should not be construed as an admission that any of the information it contains constitutes prior art against the present patent application.

SUMMARY

In the present description, the term "parameters" can refer, inter alia, to medical factors that need to be taken into consideration for selection of a medication. Namely, existence of medical results for a specific patient, within predefined ranges, would contraindicate administration of a specific drug, and other medical results indicate that a drug is excellent for treatment; such medical results are termed "parameters" for selection of a drug.

Aspects of embodiments provide a computerized method of selecting an optimal medication for a patient, comprising:
providing a user with communication access to a central server having in memory a database of a rule set associated with a list of medications available, the rules set numerically ranking the suitability of a medication for a patient; allowing upload of at least a portion of an electronic medical record for an identified patient;
allowing input of a patient diagnosis, and receiving a search request for a suitable treatment medication;
comparing the rules set, with the uploaded electronic medical record; scoring and calculating the suitability of medications from the list of medications available;
providing a displayable list of medications suited for the patient, wherein the list is ranked according to the preference of the medications for the patient.

Preferably, the rule set comprises medical parameters which influence the suitability of the medication.

Embodiments further provides a computerized system for selecting an optimal medication for a patient, the system comprising:
an input interface configured to:
receive at least a portion of an electronic medical record for an identified patient; allow input of a patient diagnosis;
receive a search request for a suitable treatment medication from a user; a processing unit operatively connected to the input interface;
a storage unit operatively connected to the processing unit to store the input data;
the storage unit storing a database of a rule set associated with a list of medications available, the rules set numerically ranking the suitability of a medication for a patient;
the storage unit also containing instructions that when executed by the processing unit cause the processing unit to:
compare the rules set, with the received electronic medical record;
determine the suitability of medications from the list of medications available;
provide a displayable list of medications suited for the patient, wherein the list is ranked according to the preference of the medications for the patient.

Still further, embodiments disclose a non-transitory and/or a transitory machine readable storage medium containing instructions associated with tracking production in a production facility and obtaining searchable production records; the instructions when executed cause the processor to execute the following:
receive at least a portion of an electronic medical record for an identified patient;
allow input of a patient diagnosis;
receive a search request for a suitable treatment medication from a user;
compare a rules set, with the received electronic medical record; wherein the rule set is associated with a list of medications available, the rules set numerically ranking the suitability of a medication for a patient;
determine (e.g., score and calculate) the suitability of medications from the list of medications available;
provide a displayable list of medications suited for the patient, wherein the list is ranked according to the preference of the medications for the patient.

This summary introduces a selection of concepts in a simplified form that are further described below in the Description of the Figures and the Detailed Description. This summary is not intended to identify key features or essential features of the claimed subject matter, nor is it intended to be used to limit the scope of the claimed subject matter

BRIEF DESCRIPTION OF THE DRAWINGS

Embodiments are illustrated by way of example in the figures of the accompanying drawings, in which like references indicate similar elements and in which:

FIG. 7 is a schematic illustration of a screen allowing a physician to type in the latest medical data values received for a specific patient.

FIG. 8 is a schematic illustration of a screen of a final outputted list of recommended medications, ranked in order of their suitability for treatment, according to some embodiments;

FIG. 9 is a schematic illustration of rules and scoring logic of the system and method for several example medications for treatment of diabetes, according to some embodiments.

DETAILED DESCRIPTION

Figure 1:
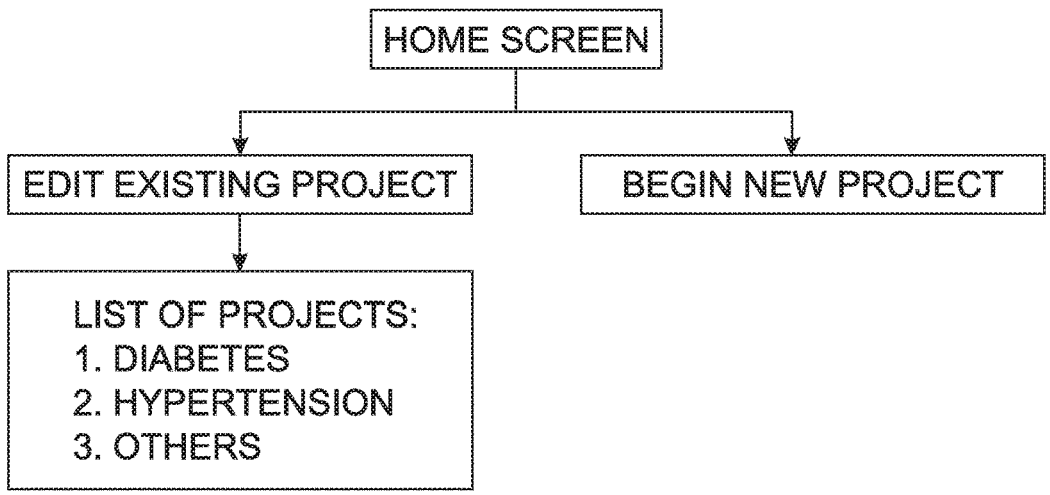
FIG. 1 illustrates a flow chart showing use by an administrator of the system, according to some embodiments.

It is an object to provide a computerized system and method of selecting an optimal medication for a specific patient, which takes into account the patient's known medical history and/or of other patients. The system and method utilizes, in an embodiment, a rules set and scoring system to rank the suitability of various medications for each patient, according to the patient medical history from his medical electronic record (MER). The system outputs a scored list of optimal medications which are most suited for prescription.

Aspects of embodiments may thus relate to methods and systems that allow automatically choosing medications for a specific disease according to specific criteria to shorten the length of time needed to select an optimal medication for a specific patient with a known diagnosis.

In the following detailed description, numerous specific details are set forth in order to provide a thorough understanding of the embodiments. There is no intention to limit the invention to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

In a general overview, the embodiments provide a system and method implementing, e.g., a software application, for selecting an optimal medication for a specific patient. During a doctor-patient appointment, the physician will enter a diagnosis into the system running the application or engine of the invention, in order to receive a recommended medication for treatment.

The term "engine" may comprise one or more computer modules, wherein a module may be a self-contained hardware and/or software component that interfaces with a larger system. A module may comprise a computer-readable and machine or machines executable instructions. A module may be embodied by a circuit or a controller programmed to cause the system to implement the method, process and/or operation as disclosed herein. For example, a module may be implemented as a hardware circuit comprising, e.g., custom VLSI circuits or gate arrays, an Application-specific integrated circuit (ASIC), off-the-shelf semiconductors such as logic chips, transistors, and/or other discrete components. A module may also be implemented in programmable hardware devices such as field programmable gate arrays, programmable array logic, programmable logic devices and/or the like.

The system and method takes into account the patient's medical results as they appear in the patient's electronic medical record, to detect "parameters of interest".

A rule set indicates and determines which parameters are acceptable for each medication, and which parameters prevent prescription of the medication.

The rules set and parameters associated with the medications, are stored as a database located on one or more central servers that are in communication with the computer terminals used by the various end user physicians.

In an embodiment, the rule set relate to vales of medical parameters which can influence the suitability of the medication.

The system and method of the invention utilize as input: the specific patient parameters (medical results for the individual patient) and the physician's diagnosis.

The system and method utilizes the rule set, and ranks the available medications from the database, in order of their preference for the specific patient medical data, and displays a scored list according to optimal medication.

The scored list of optimal medications, represents the latest medical board recommendations, which tend to change periodically. Thus, any physician's treatment plan is upgraded to be the best care available.

The system and method can prevent harmful drug interactions in complex patients having other chronic prescriptions, and prevents prescription of medications which are contraindicated due to specific patient medical data.

Optionally, the rules set may establish preferences for generic medications or for those approved by the HMO.

In an embodiment, the medical history is automatically obtained from the patient's electronic medical record (EMR), without the need for the physician to type in data other than the date of visit, symptoms, and diagnosis.

In another embodiment, the method utilizes big data analysis of all patient medical data available, in order to detect the treatment success rate of a specific medication, and marks highly successful medications as preferred for recommending to future patients. Thus, machine learning produces constant improvement of the final outputted product list of recommended medications; as new data including treatment success rates, is collected constantly and is used as the input for each software run.

Referring now to FIG. 1, a flow chart is shown illustrating use by an administrator of the system, according to some embodiments. The administrator may choose between entering rules for a disease new to the system ("new project") and/or may choose to view or edit rules for diseases or medications already in the system ("Edit Existing Project"). Examples of projects already in the system include Diabetes and hypertension.

Figure 2:
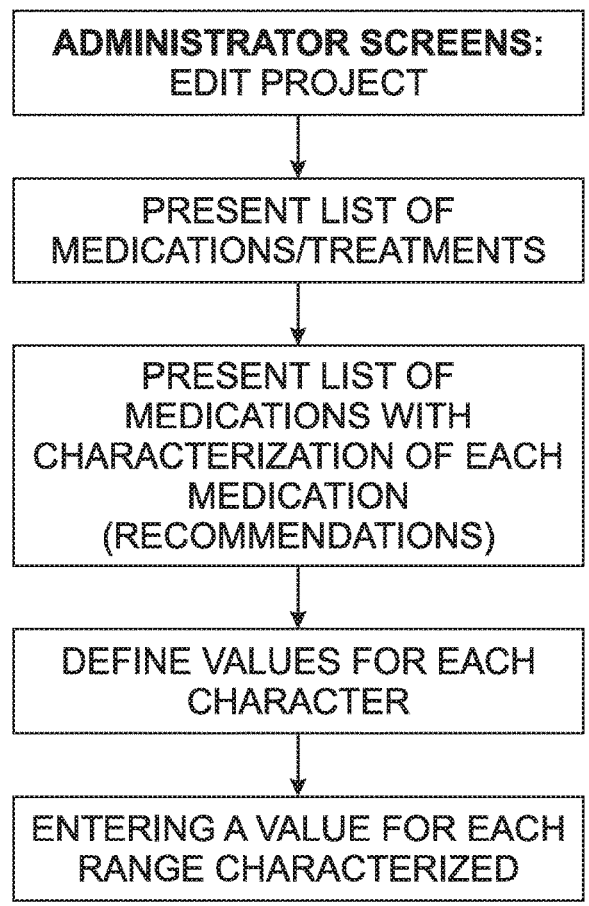
FIG. 2 is an administrator flowchart showing how an administrator may open a known project and add rules associated with a medication into the system, according to some embodiments.

Referring to FIG. 2, the administrator has selected to edit a project already saved in the database of the system. The administrator may choose to ask for display of a list of medications available, with the rules associated with prescribing each medication ("characterization of parameters of each medication and recommendations"). If such rules are not yet in the system, the administrator may enter them now.

Examples of such rules may be "contraindicated for obese patients", "recommended highly for ages 20-40", "contraindicated in combination with medication X", etc., and may include dosage instructions as well The rules may be dependent on specific parameter values measured for a patient, as appearing in his medical history, such as "only recommended for patients having a BMI between values of 18-25", "only prescribe to nondiabetics with a proven fasting glucose of 4.0 to 6.0 mmol/L (72 to 108 mg/dL)", etc.

The administrator may then choose to edit the rules for a medication, according to latest medical studies, according to the local board of health recommendations, or according to the HMO recommendations.

The administrator may tailor the system and method to suit the directives given to local practitioners, by choosing for instance, to rank the importance of a parameter according to recommendations given by the Mayo clinic, while in another instance he may use NIH recommendations for another parameter.

The administrator may also tweak the rage of acceptable values for any parameters of interest. The acceptable range of a parameter, or its importance, may change over time according to the latest medical data.

The administrator may choose to enter a new medication for treatment of a disease that is already in the database ("known project, new medication"). He will then define the rules and parameters which are associated with the medication, and which define which patients it is best suited. The rules and parameters are saved to a central database.

Figures 3, 4:
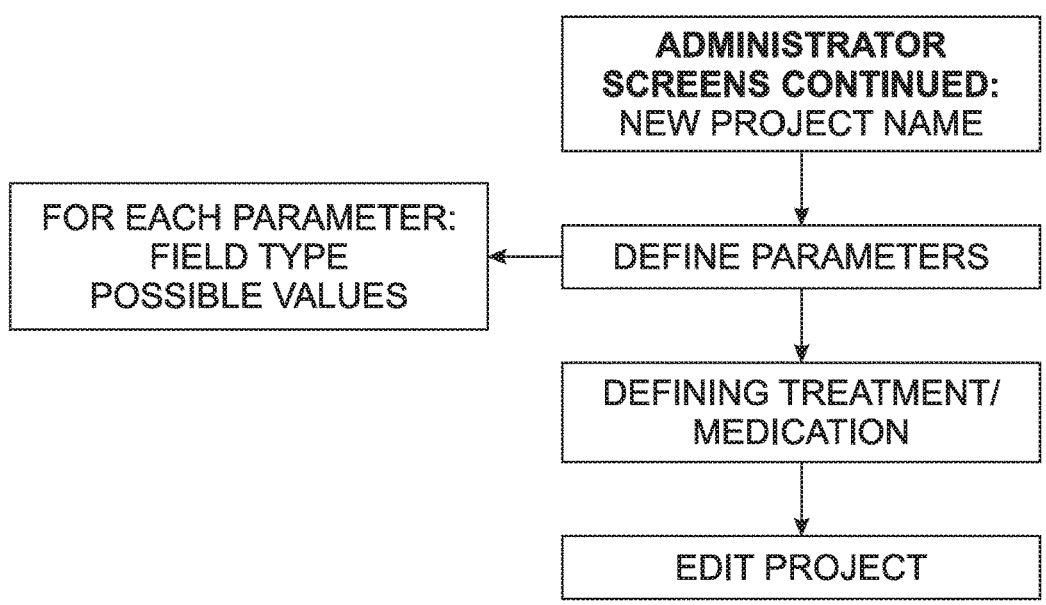
FIG. 3 is a schematic screenshot illustration showing how the administrator adds rules and parameters associated with the medication, according to some embodiments.
FIG. 4 is an administrator flowchart, allowing an administrator to enter rules and parameters for a medication or treatment which are new to the system, according to some embodiments.

Referring to FIG. 3, a screenshot is shown of the administrator screen for an entering rules and parameters for a new medication.

The disease name is entered, and a description of its central symptoms.

A list of medications which may be used to treat the disease appears under the heading "Treatments Associated with the Disease". In FIG. 3, the disease entered was Diabetes, and a list of possible medications which may be prescribed was retrieved from the central database (e.g. Acarbose™ Actose™, etc.).

When the administrator clicks on a specific medication, such as Acarbose™, the software will display a list of parameters which effect whom the medication is best recommended for. These will be displayed under the heading "Parameters Associated with the Disease".

The administrator may press the "Enter Rules" button, and then enter the recommended values for each parameter that influences the decision on whether the medication is optimal for administration to a specific patient.

For instance, Age is one parameter shown, and the administrator will enter the optimal range of ages recommended for each medication. The administrator will press the "Save" button to save the rules entered.

Non-limiting examples of parameters which may affect the rules set and therefore are used by the invention to rank their relevance for a specific patient, include: Age, Gender, BMI, HBA1C levels, Abnormal Creatinine levels, eGFR (estimated glomerular filtration rate) levels, pancreatitis, hypoglycemia, fasting glucose, post prandial glucose, thyroid cancer, gastroparesis, gentiourinary infection, ischemic heart disease, stroke, hypertriglyciredemia, bladder cancer, and osteoporosis.

The administrator defines the importance of each parameter by entering an importance ranking for the parameter. The importance of each parameter is dependent on the specific mediation, and can differ, as shown by clinical studies. For instance, administration out of the recommended age range may be fatal in one medication, yet may be less important in another medication. Similarly, drug interactions may be dangerous in one combination, while may be minor in another. The administrator therefore ranks the importance of the parameter, according to the severity of the possible consequences of nonadherence to a recommendation related to the parameter. The importance may be ranked numerically on a scale of 1-10, or may be in the form of "High-Medium-Low".

The quality, efficacy and safety of a treatment may be ranked to assign their importance, and the cost may be ranked according to its relative importance in the decision making process.

There may be highly specific ranges of values that are considered preferred values for a parameter. For instance, an age of 52-55 may be highly optimal for a specific medication.

The rule set indicates and determines which parameters are acceptable for each medication, and which parameters prevent prescription of the medication. The rules set and parameters associated with the medications, are stored in a database located on one or more central servers that are in communication with the computer terminals used by the various end user physicians.

Referring now to FIG. 4, an administrator flowchart is shown, allowing an administrator to enter rules and parameters for a medication or treatment which are new to the system.

Figure 5:
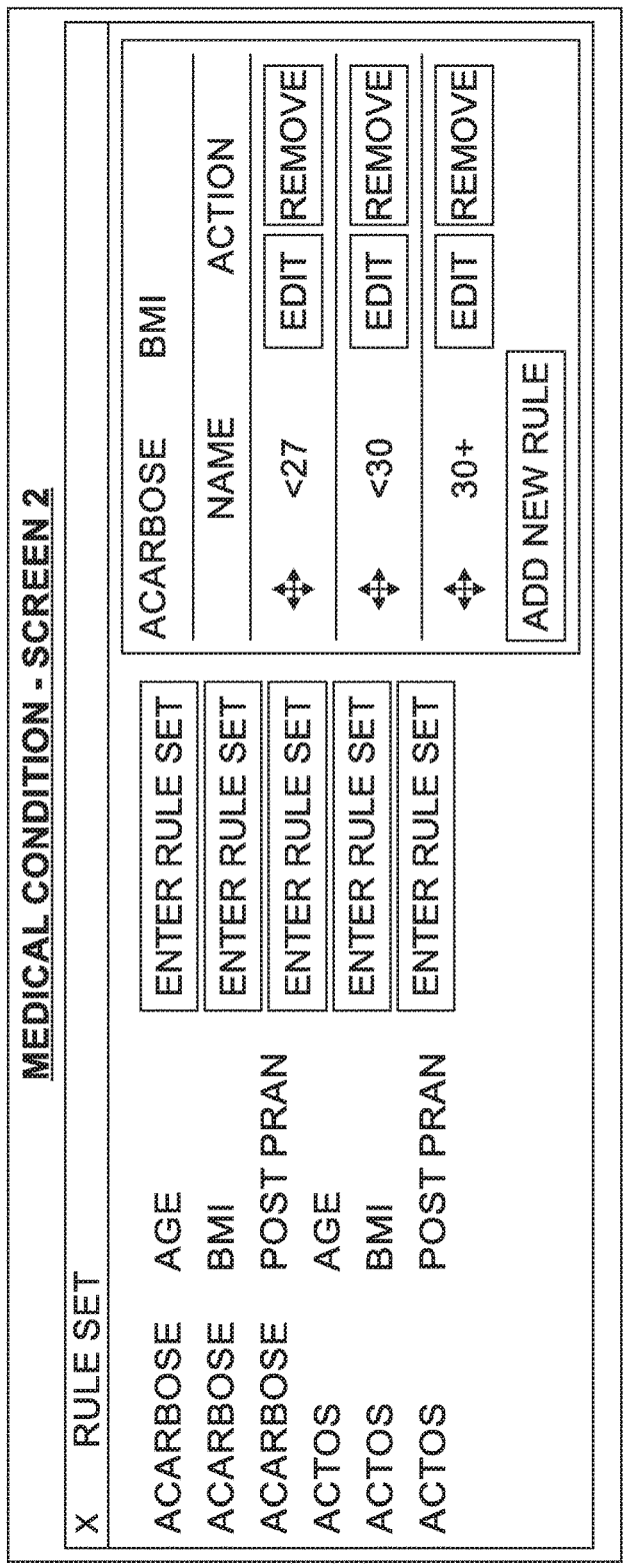
FIG. 5 is a schematic illustration of a screen for an administrator for entering rules associated with the medications Acarbose™ and Actose™, according to some embodiments.

Referring to FIG. 5, a screenshot is shown for an administrator for entering rules associated with the medications Acarbose™ and Actose™. The parameters which effect the rules for prescription of these medications, are shown at left, and include Age, BMI and the Postprandial Glucose Level ("Post Pran"). The administrator may enter the recommended levels of these parameters, for prescribing Acarbose™ or Actose™, by clicking on the "Enter Rules Set" button adjacent to each parameter.

The screen at the right of FIG. 5 will then open, allowing the administrator to enter a rule for how BMI<27 effects the prescription of Acarbose™, another rule for how BMI<30 effects the prescription of Acarbose™, etc.

The administrator may add another new rule, by clicking on the "Add New Rule" button on the bottom of the right screen.

Figure 6:
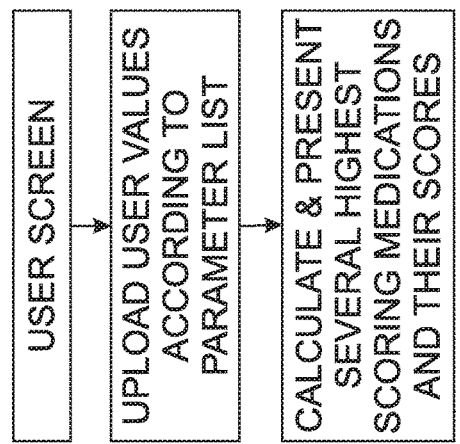
FIG. 6 is a flowchart is shown for presenting flow of information for an end user physician, according to some embodiments.

Referring to FIG. 6, a flowchart is shown for flow of information for an end user physician. During a patient visit, the physician opens the patient's electronic medical record (EMR) and records the patient's chief complaint, symptoms and date of visit. If a physical examination is required, the physician will perform one, and will enter his diagnosis into the patient's electronic medical system. The physician will then run the application to select an optimal medication to prescribe from among many that are available.

In an embodiment, the parameters that effect selection of a medication are automatically uploaded to the system, without requiring the physician to type them in.

In other embodiments, the physician will be prompted to type in the latest values for parameters that are important for the selection decision.

In addition to the latest laboratory results, the system and method may take into account additional patient specific medical history, when determining the suitability of a medication. This medical data may be found in the patient's electronic medical record, and may for example include: history of present illness, past medical history, past surgical history, family history, social history, medications, allergies, review of symptoms, vital signs, physical exam, and/or diagnostic tests.

The physician will then click on "calculate" to receive a scored list showing the five most preferred medications available, and the numerical preference score they received by the system, in order of preference.

Referring now to FIG. 7, a screen is schematically shown in which a physician has been prompted to type in the latest medical data values received for a specific patient, for parameters that are important for selecting an optimal medication. In this instance, the physician evaluating patient John Smith, has entered the following values measured for the patient: age=58, BMI=32, GFR=75, UTI (suffers from UTI=1), pancreatitis (does not suffer from pancreatitis=0).

The physician will then click on the "calculate" button, to receive a ranked list of preferred medications to prescribe, as shown in FIG. 8.

Referring to FIG. 8, a screenshot is shown, of the final outputted list of recommended medications, ranked in order of their optimal suitability for treatment, and including the score obtained for each medication. Treatment Medication D appearing at the top of the list is most preferred, and received the highest score (100), followed by Treatment Medications C (score 82), then A (score 65). Thus Treatment A only appears as a Secondary Recommendation, and will only be prescribed if the top choices D or C are unavailable.

Treatment F (score 23) shows "contraindicated", and the least recommended medication is Treatment B (score 10) appears at the bottom of the list, and is contraindicated.

The physician is provided with several options, and their scores, in case the best option is temporarily unavailable or is not covered by the patient's HMO. The physician can then view the score of the next medication on the list and can determine if the medications are relatively interchangeable, or if there is a considerable drop in the preference rate, and can then suggest the patient pay privately for the optimal medication or switch to the best medication when it becomes available on the market.

If a medication is deemed highly contraindicated for the patient, a highly visible "Danger" icon will appear adjacent to the specific treatment medication, in the outputted list, in addition to the relatively low score, to prevent accidental prescription of the medication in a busy physician's office. In FIG. 8, Treatment B which scored 10 would be thus indicated.

Referring to FIG. 9, the rules and scoring logic of the method and system are illustrated for several medications for treatment of diabetes.

The patient age is not relevant for three of the medications listed (Acarbose, Actos, Byetta), so that the age scoring will be 0 for these medications. However, a dangerous age bracket exists for Amaryl, it is not recommended for patients over the age of 60, giving a −1 score for any patient in that age bracket for Amaryl.

For a patient having a BMI of 30+, Acarbose and Byetta are most suited, as shown by the score of +2, while Amryl is least suitable for this BMI, as shown by the score of −2.

Patients having HBA1C measurements of +7.5 will benefit the most from Byetta, as shown by the scoring of 2, while an HBA1C measurement of 10+ prevents prescription of Acarbose, as shown by the scoring of −2.

An elevated post prandial glucose measurement ("Post Pran. Yes") for a patient, signifies patient suitability for Acarbose, Amaryl or Byetta, as shown by the score of 2 for these medications. In contrast, the decision of whether to prescribe Actose is not influenced by the post prandial glucose measurement (scoring 0).

In an embodiment, the invention utilizes big data analysis of all patient medical data available, in order to detect the treatment success rate of a specific medication, and marks highly successful medications as preferred for recommending to future patients.

Thus, machine learning produces constant improvement of the final outputted product list of recommended medications; as new data including treatment success rates, is collected constantly and is used as the input for each software run.

In an embodiment, parameters are pre-marked in the database when shown to be typically most important to selecting the medication for a diagnosis. These may be selected based on their being frequently used parameters, for a particular area of therapy or indication. Then, during use of the invention, these parameters will be run first in order to speed up the run-time of the scoring and calculation for a specific patient.

The following are non-limiting examples of well-known medications which may be selected from for treatment of diabetes, using the computerized system and/or method to select the optimal medication for a specific patient:

Gluben, gluco-rite, amaryl, novonorm, prandase, actos, Januvia, januet, trajenta, trajents duo, onglyza, combiglyza, galvus, eucreas, byetta, bydureon, lyxumia, victoza, trulicity, forxiga, xigduo, jardiance, jardiance duo, glyxambi, xultophy, insulin.

Examples of patient medical parameters that may affect the selection of the above medications, include: Age, BMI, HBA1C levels, Abnormal Creatinine levels, eGFR (estimated glomerular filtration rate) levels, pancreatitis, hypoglycemia, fasting glucose, post prandial glucose, thyroid cancer, gastroparesis, gentiourinary infection, ischemic heart disease, stroke, hypertriglyciredemia, bladder cancer, and osteoporosis.

The system includes a processing unit, a storage unit, an input interface, and an output interface. In this embodiment, these components are part of a personal computer, and they form a computing module. The components instead may be part of a workstation, PDA, or smart phone as non-limiting alternative example embodiments.

The input interface of the computerized system is configured to receive of at least a portion of an electronic medical record for an identified patient, and receives a patient diagnosis, and receives and stores data pertaining to the database comprising the rule set associated with a list of medications available, in a storage unit having digital memory. The input interface may for example include a USB socket of the personal computer. The input interface may alternatively receive input from an entry device, such as a keyboard, and/or adjacent computer systems, such as an electronic medical record (EMR) database. The computerized system includes an input module that is configured to transmit to the input interface a user's input.

The processing unit is operatively connected to the graphic input interface, the output interface, and the storage unit. The processing unit executes instructions contained in the storage unit. The instructions, when executed, cause the processing unit to:

provide a user with communication access to a central server having in memory a database of a rule set associated with a list of medications available, the rules set numerically ranking the suitability of a medication for a patient;

allow upload of at least a portion of an electronic medical record for an identified patient;

allow input of a patient diagnosis, and receiving a search request for a suitable treatment medication;

compare the rules set, with the uploaded electronic medical record;

determine, based on the rules set, the suitability of medications from the list of medications available;

provide a displayable list of medications suited for the patient, wherein the list is ranked according to the preference of the medications for the patient.

As non-limiting examples, the processing unit of system may include an Intel Pentium Processor E5400, an Intel Xeon 5130 CPU, or any other equivalent means for processing (executing) instructions contained in the storage unit. Also, as non-limiting examples, the storage unit 14 may be SATA hard drive, a flash memory SSD, or any other equivalent means for storing instructions that when executed by the processing unit cause the processing unit to function as described above.

The embodiment may be modified to allow a user to interact with a computing module through a network. As non-limiting examples, the network may be a local area network (LAN) within an office environment or alternatively the Internet. An alternative embodiment may implement a "hosted" architecture for the computing module, whereby the algorithmic calculations are done in a remote data-center (server farm) accessible over the network/Internet. Another alternative embodiment may implement a cloud computing configuration for the computing module. Thus, a user may interact with the computing module using a Microsoft® Windows-based utility or a web browser, as non-limiting examples.

In an embodiment, the rule set which indicates and determines which parameters are acceptable for each medication, and the list of available medications, are stored as a database located on one or more central servers that are in communication with a plurality of computer terminals used by the various end user physicians.

In terms of its systematic implementation, the embodiments suitably comprise a set of relevant databases, hosted on a computer or data processing system of suitable type. The databases are accessible to a hand-held, laptop-type or desktop-type computer display for access by a physician or clinical worker. In addition to being hosted on a local data processing machine, the databases are contemplated as being maintained in a centralized data processing server implementation, such that it is accessible through a local or wide area network for download by a physician or practice group. Maintaining the database in a centralized location allows database terminology to be maintained on a more uniform basis, thereby minimizing the present-day confusion generated by inconsistent terminology for both indications and clinically relevant diagnoses. In a manner well understood by those having skill in the art, database contents may be uploaded to the centralized server so that additions and embellishments may be provided to the centralized system by physicians that may have discovered an additional indications usage for a particular medication and who wishes to share this information with the medical community at large.

In addition to being a self-contained medical decision support system, the system also incorporates an interface to any one of a number of commercially or conventionally available electronic medical recordkeeping applications, such that as an exact diagnosis is extracted, the exact diagnosis is automatically ported to the appropriate input port of the medical records program.

In an embodiment, the data entry application, and its associated database, may be implemented as an application software program that is written with the requisite I/O "hooks", such that it can be incorporated as an "applet" and/or "servelet" in a medical recordkeeping program. As patient information is added in conventional fashion, the medical record program invokes the application system and/or method as soon as the physician reaches the "medications", "indications", and/or "diagnoses" portions of the recordkeeping program input.

The clinical decision support system thus provides an evidence-based solution that is designed to help physicians select the most appropriate medication for a specific medical condition.

This system and method of the invention are built as a flexible scoring system with an administrator layer and an end-user layer. A preference score of a specific medication may be determined by the invention, and is displayed as output, for a physician aiming to provide optimal patient treatment. The rules set, which determines the output, is based on the most updated evidence, and based on medical board recommendations and/or HMO directives. Medical criteria are determined by administrating physicians specializing in specific disease fields using evidence—based methodology.

The system chooses an optimal medication from a list of medications/treatments based on the rules set associated with a parameter list. Each parameter receives a score (and sub-score), indicating whether it affects the selection of a specific medication, and how important the influence is of the parameter to the decision making of the invention.

The end-user physician uploads the details of a patient's medical history for the relevant parameters which determine the medication (e.g. kidney function, BMI, lipid profile, etc.). The system determines the score (and sub-score) for each medication/treatment and provides a list of drugs best suited to the patient's specific medical history in ranked preference.

The system is dynamic, allowing it to be developed and used for any common disease for which treatment could be selected using a scoring system.

The methods and/or processes disclosed herein may be implemented as a computer program or computer program product tangibly embodied in an information carrier, for example, in a non-transitory tangible computer-readable or non-transitory tangible machine-readable storage device and/or in a propagated signal, for execution by or to control the operation of, a data processing apparatus including, for example, one or more programmable processors and/or one or more computers.

The terms "non-transitory computer-readable storage device" and "non-transitory machine-readable storage device" encompasses distribution media, intermediate storage media, execution memory of a computer, and any other medium or device capable of storing for later reading by a computer program implementing embodiments of a method disclosed herein. A computer program product can be deployed to be executed on one computer or on multiple computers at one site or distributed across multiple sites and interconnected by one or more communication networks.

Computer readable and executable instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable and executable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable and executable instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Although embodiments have been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. Citation or identification of any reference in this application shall not be construed as an admission that such reference is available as prior art to the present invention.

The invention claimed is:

1. A computerized method of selecting an optimal medication for a patient, comprising:
  a) providing a user with communication access to a central server having in memory a database of rule set associated with a list of possible medications, said rule set relating to the suitability of a possible medication for an identified patient;
  b) allowing identification of at least a portion of an uploaded electronic medical record for the identified patient and general patients;
  c) allowing input of the identified patient diagnosis, and receiving a search request for a suitable possible medication;
  d) comparing said rule set, with said uploaded electronic medical record in order to detect a suitability of treatment of a specific possible medication;
  e) determining, based on said rule set comparison with the uploaded electronic medical record, the suitability of the possible medication from said list of possible medications;
  f) determining a score for said list of possible medications according to the suitability of treatment of said medications for said identified patient;
  g) providing a displayable list of possible medications suited for said identified patient, wherein said list of possible medications is numerically ranked according to the score of the suitability of treatment of said medications for said identified patient; and
  i) providing, based on the score, location-dependent directives to local practitioners.

2. The method of claim 1, wherein said rule set comprises medical parameters which influence the suitability of said medications.

3. The method of claim 2, wherein said medical parameters are selected from at least one of: age, gender, BMI, HBA1C levels, creatinine levels, estimated glomerular filtration rate levels, pancreatitis, hypoglycemia, fasting glucose, post prandial glucose level, thyroid cancer, gastroparesis, gentiourinary infection, ischemic heart disease, stroke, hypertriglyciredemia, bladder cancer, and osteoporosis.

4. The method of claim 2, wherein said medical parameters comprise medical data values which indicate a preference for a specific possible medication.

5. The method of claim 2, wherein predefined medical parameters are marked in said rule set as most important to selecting a possible medication.

6. The method of claim 5, wherein said predefined medical parameters are determined prior to other unmarked medical parameters to allow fast run-time.

7. The method of claim 1, wherein said rule set comprises an importance factor for each rule, defining the relative weight of said rule in said step of determining a score.

8. The method of claim 1, wherein said electronic medical record is uploaded automatically without the need for a user physician to type in data.

9. The method of claim 1, wherein said rule set comprises a list of contraindications for prescribing a medication, associated with each possible medication.

10. The method of claim 1, wherein said rule set is adjustable by an administrator, allowing tailoring of said rule set to latest medical knowledge.

11. The method of claim 1, wherein said electronic medical record of a patient comprises at least one of: history of present illness, past medical history, past surgical history, family history, social history, medications, allergies, review of symptoms, vital signs, physical exam, and diagnostic tests.

12. The method of claim 1, wherein in displayable list of possible medications, a highly visible icon will be displayed adjacent to any medication deemed highly contraindicated for a patient.

13. A computerized system for selecting an optimal possible medication for a patient, said system comprising:
  an input interface configured to:
    receive at least a portion of an electronic medical record for an identified patient and general patients;
    allow input of a patient diagnosis;
    receive a search request for a suitable possible medication from a user;
  a processing unit operatively connected to the input interface;
  a storage unit operatively connected to the processing unit to store the input data;
  said storage unit storing a database of a rule set associated with a list of possible medications, said rule set numerically ranking the suitability of a possible medication for the identified patient;
  the storage unit also containing instructions that when executed by the processing unit cause the processing unit to:

compare said rule set, with said received electronic medical record;

determine, based on said rules set comparison with the received electronic medical record, the suitability of the possible medication from said list of possible medications for the identified patient;

determine a score for said list of possible medications according to the suitability of treatment of said medications for said identified patient; and provide a displayable list of possible medications suited for said identified patient, wherein said list of possible medications is numerically ranked according to the score of the suitability of treatment of said possible medications for said identified patient, and provide, based on the score, location-dependent directives to local practitioners.

14. The system of claim 13, wherein said displayable numerically ranked list of possible medications provides the user an ability to compare between alternative possible medications with regard to their availability.

15. The system of claim 13, wherein said displayable numerically ranked list of possible medications provides the user an ability to compare between alternative possible medications with regard to the identified patient's health maintenance organization (HMO) insurance coverage.

16. The system of claim 13, wherein the user is automatically prompted to provide additional data to said uploaded electronic medical record in order to optimize the possible medication selection process.

17. The method of claim 13, wherein said location-dependent directives are based on the ranking of parameters provided by different maintenance organization (HMO) recommendations.

18. A non-transitory machine readable storage medium containing instructions associated with tracking production in a production facility and obtaining searchable production records; the instructions when executed cause the processor to execute the following:

receive at least a portion of an electronic medical record for an identified patient and general patients;

allow input of the identified patient diagnosis;

receive a search request for a suitable possible medication from a user; compare a rule set, with said received electronic medical record; wherein said rule set is associated with a list of possible medications, said rule set numerically ranking the suitability of a possible medication for a patient;

determine, based on said rule set comparison with the received electronic medical record for the identified patient, the suitability of said possible medication from said list of possible medications for the identified patient;

determine a score for said list of possible medications according to the suitability of treatment of said medications for said identified patient;

provide a displayable list of possible medications suited for said identified patient, wherein said list of possible medications is numerically ranked according to the score of the suitability of treatment of said possible medications for said identified patient; and provide, based on the score, location-dependent directives to local practitioners.

* * * * *